(12) United States Patent
Moly et al.

(10) Patent No.: US 12,059,258 B2
(45) Date of Patent: Aug. 13, 2024

(54) METHOD FOR CALIBRATING ON-LINE AND WITH FORGETTING FACTOR A DIRECT NEURAL INTERFACE WITH PENALISED MULTIVARIATE REGRESSION

(71) Applicant: COMMISSARIAT A L'ENERGIE ATOMIQUE ET AUX ENERGIES ALTERNATIVES, Paris (FR)

(72) Inventors: Alexandre Moly, Grenoble (FR); Tetiana Aksenova, Grenoble (FR); Alexandre Aksenov, St Egreve (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 389 days.

(21) Appl. No.: 17/450,601

(22) Filed: Oct. 12, 2021

(65) Prior Publication Data

US 2022/0110570 A1 Apr. 14, 2022

(30) Foreign Application Priority Data

Oct. 14, 2020 (FR) ...................................... 20 10497

(51) Int. Cl.
*A61B 5/279* (2021.01)
*G06F 3/01* (2006.01)
*G06V 10/75* (2022.01)

(52) U.S. Cl.
CPC .............. *A61B 5/279* (2021.01); *G06F 3/015* (2013.01); *G06V 10/75* (2022.01); *A61B 2560/0228* (2013.01)

(58) Field of Classification Search
None
See application file for complete search history.

(56) References Cited

U.S. PATENT DOCUMENTS

2019/0320924 A1\* 10/2019 Yelisyeyev .............. A61B 5/24

FOREIGN PATENT DOCUMENTS

| FR | 3 046 471 A1 | 7/2017 |
|---|---|---|
| FR | 3 061 318 A1 | 6/2018 |

(Continued)

OTHER PUBLICATIONS

French Preliminary Search Report issued Jun. 29, 2021 in French Application 20 10497 filed on Oct. 14, 2020, therein, 2 pages (with English Translation of Categories of Cited Documents).

(Continued)

*Primary Examiner* — Ankit D Tejani
(74) *Attorney, Agent, or Firm* — Oblon, McClelland, Maier & Neustadt, L.L.P.

(57) ABSTRACT

The present invention relates to a method for calibrating on-line a direct neural interface implementing a REW-NPLS regression between an output calibration tensor and an input calibration tensor. The REW-NPLS regression comprises a PARAFAC iterative decomposition of the cross covariance tensor between the input calibration tensor and the output calibration tensor, each PARAFAC iteration comprising a sequence of M elementary steps ($240_1$, $240_1$, ... $240_M$) of minimisation of a metric according to the alternating least squares method, each elementary minimisation step relating to a projector and considering the others as constant, said metric comprising a penalisation term that is a function of the norm of this projector, the elements of this projector not being subjected to a penalisation during a PARAFAC iteration f not being penalisable during following PARAFAC iterations. Said calibration method makes it possible to obtain a predictive model of which the non-zero coefficients are sparse blockwise.

7 Claims, 3 Drawing Sheets

(56) References Cited

FOREIGN PATENT DOCUMENTS

WO     WO 2011/144959 A1     11/2011
WO     WO-2018122518 A1 *     7/2018     ............... A61B 5/24

OTHER PUBLICATIONS

Eliseyev et al., "Recursive Exponentially weighted N-way partial least squares regression with recursive-validation of hyper-parameters in brain-computer interface applications", Scientific Reports, vol. 7, No. 1, 2017, 15 pages, XP055705682.
Cichocki et al., "Fast Local Algorithms for Large Scale Nonnegative Matrix and Tensor Factorizations", IEICE Transactions of Fundamentals of Electronics, vol. E92-A, No. 3, Mar. 2009, 14 pages, XP001544993.
Eliseyev et al., "Recursive N-Way Partial Least Square for Brain-Computer Interface", PLOS One, vol. 8, issue 7, Jul. 2013, 13 pages, XP055178425.
Kimura, "A Study on Efficient Algorithms for Nonnegative Matrix/Tensor Factorization", Mar. 23, 2017, 116 pages, XP055819105.
Eliseyev et al., "L1-penalized N-way PLS for subset of electrodes selection in BCI experiments", J. Neural Eng., vol. 9, No. 4, 2012, 15 pages.

* cited by examiner

METHOD FOR CALIBRATING ON-LINE AND WITH FORGETTING FACTOR A DIRECT NEURAL INTERFACE WITH PENALISED MULTIVARIATE REGRESSION

TECHNICAL FIELD

The present invention relates to the field of direct neural interfaces, also called BCI (Brain Computer Interfaces) or BMI (Brain Machine Interfaces). It is notably applied to the direct neural command of a machine, such as an exoskeleton or a computer.

PRIOR ART

Direct neural interfaces use the electrophysiological signals emitted by the cerebral cortex to elaborate a command signal. These neural interfaces have been the subject of numerous research notably with the aim of restoring a motor function to a paraplegic or tetraplegic subject using a motorised prothesis or orthosis.

Neural interfaces may be of invasive or non-invasive nature. Invasive neural interfaces use intracortical electrodes (that is to say implanted in the cortex) or cortical electrodes (arranged on the surface of the cortex) collecting in this latter case electrocorticographic (ECoG) signals. Non-invasive neural interfaces use electrodes placed on the scalp to collect electrocephalographic (EEG) signals. Other types of sensors have also been envisaged such as magnetic sensors measuring the magnetic fields induced by the electrical activity of the neurones of the brain. One then speaks of magnetocephalographic (MEG) signals.

Direct neural interfaces advantageously use ECoG type signals, having the advantage of a good compromise between biocompatibility (matrix of electrodes implanted on the surface of the cortex) and quality of the collected signals.

The ECoG signals thus measured must be processed in order to estimate the trajectory of the movement desired by the subject and to deduce therefrom the command signals of the computer or of the machine. For example, when it involves commanding an exoskeleton, the BCI estimates the trajectory of the desired movement from measured electrophysiological signals and deduces therefrom the control signals enabling the exoskeleton to reproduce the trajectory in question. Similarly, when it involves commanding a computer, the BCI estimates for example the desired trajectory of a pointer or a cursor from electrophysiological signals and deduces therefrom the command signals of the cursor/pointer.

The estimation of trajectory, and more specifically that of kinematic parameters (position, speed, acceleration), is also designated neural decoding in the literature. Neural decoding notably makes it possible to command a movement (of a prothesis or a cursor) from ECoG signals.

The estimation of trajectory and the calculation of signals for controlling the exoskeleton or the effector generally requires a prior learning or calibration phase, designated off-line. During this phase, the subject imagines, observes or makes a movement according to a determined trajectory during a given calibration interval. The electrophysiological signals measured during this interval are exploited in relation with this trajectory to construct a predictive model and more specifically to calculate the parameters of this model.

The validity of the predictive model is however limited in time on account of the non-stationarity of the neural signals. For this reason, it is necessary to carry out an on-line calibration of the predictive model, that is to say as and when the neural signals are observed and the command applied.

Different methods for calibrating on-line a neural interface have been described in the prior art. However, these on-line calibration methods may require the manipulation of a considerable amount of data resulting from the juxtaposition of data from prior calibration steps and those from a new calibration step.

An on-line BCI calibration method has been described in the article of A. Eliseyev et al. entitled "Recursive exponentially weighted N-way Partial Least Squares regression with recursive validation of hyper-parameters in Brain-Computer Interface applications" published in Scientific Reports, vol. 7, no 1, p. 16281, November 2017 as well as in the patent application FR-A-3 061 318. This method will be designated hereafter under the acronym REW-NPLS (Recursive Exponentially Weighted N-way Partial Least Squares).

Furthermore, different alternatives of off-line calibration method have been proposed in the literature, with the aim of improving the robustness of the prediction and to increase the sparsity of non-zero coefficients in the predictive model tensor. In particular, the sparsity of non-zero coefficients in the spatial mode of this tensor makes it possible to only select certain relevant electrodes for the prediction of the trajectory and the calculation of the command. Such an alternative using a penalised multipath regression with such an aim has been described in the article of A. Eliseyev et al. entitled "L1-penalised N-way PLS for subset of electrodes selection in BCI experiments" published in J. Neural Eng. vol. 9, no 4, p. 045010 as well as in the patent application FR-A-3 046 471.

However, such a calibration method using a penalised multipath regression cannot be implemented on-line on account of the considerable amount of calculations that it requires.

The subject matter of the present invention is consequently to propose a method for calibrating on-line a direct neural interface that can also increase the sparsity of non-zero coefficients of the prediction tensor, notably in such a way as to only select at each observation window a relevant sub-set of electrodes.

DESCRIPTION OF THE INVENTION

The present invention is defined by a method for calibrating on-line a direct neural interface intended to receive a plurality of electrophysiological signals during a plurality of observation windows associated with observation times, to form an input tensor and to deduce therefrom, by means of a predictive model, an output tensor providing command signals intended to command one or more effectors, said calibration is carried out during a plurality of calibration steps, each calibration step u being carried out from input calibration data, represented by an input calibration tensor, $\underline{X}_u \in \square^{(I_1 \times \cdots \times I_N)}$, and from output calibration data represented by an output calibration tensor $\underline{Y}_u \in \square^{(J_1 \times \cdots \times J_M)}$, said calibration step implementing a REW-NPLS regression comprising:

the calculation of a covariance tensor $\underline{XX}_u$ from a covariance tensor $\underline{XX}_{u-1}$ obtained during a preceding calibration step and the tensor $\underline{X}_u$, as well as the calculation of a cross covariance tensor $\underline{XY}_u$ from a cross covariance tensor $\underline{XY}_{u-1}$ obtained during said preceding calibration step and the tensors $\underline{X}_u$ and $\underline{Y}_u$;

a PARAFAC iterative decomposition of the cross covariance tensor $\underline{XY}_u$, each PARAFAC iteration being associated with a dimension f of the latent variables space on which said regression is carried out, each iteration providing a plurality of projectors $w_f^i$, i=1, . . . , M of respective sizes $I_1, I_2, \ldots I_M$ and a predictive model defined by a prediction coefficients tensor $\underline{B}_u^f \in \square^{(I_1 \times \ldots \times I_M) \times (J_1 \times \ldots \times J_M)}$ and a bias tensor $\underline{\beta}_u^f \in \square^{(J_1 \times \ldots \times J_M)}$.

Said calibration method is original in that each PARAFAC iteration comprises a sequence of M elementary steps of minimisation of a metric according to the alternating least squares method, each elementary minimisation step relating to a projector and considering the others as constant, said metric comprising a penalisation term that is a function of the norm of this projector, the elements of this projector not being subjected to a penalisation during a PARAFAC iteration f not being penalisable during following PARAFAC iterations.

Advantageously, an elementary minimisation step relating to a projector $w_f^i$ aims to minimise the penalised metric $$\min_{\tilde{w}_f^i}\left(\left\|\underline{XY}_{u(i)} - \tilde{w}_f^i\left(w_f^M \otimes \ldots w_f^{i+1} \otimes w_f^{i-1} \otimes \ldots \otimes w_f^1\right)^T\right\|^2 + \lambda_i \left\|\tilde{w}_f^i\right\|_{q,\Omega_{i,f}}\right)$$

where $\tilde{w}_f^i$ is a non-normalised projector and $$w_f^m = \frac{\tilde{w}_f^m}{\|\tilde{w}_f^m\|},$$

m=1, . . . ; m≠i are normalised projectors, $\underline{XY}_{u(i)}$ is a matrix of size $$I_i \times \prod_{\substack{n=1 \\ n \neq i}}^{N} I_n$$

obtained by deployment of the cross covariance tensor $\underline{XY}_u$ while taking the mode i as reference, $\otimes$ is the Kronecker product, $\lambda_i$ is a strictly positive coefficient, $\|w\|_{q,\Omega_{i,f}}$, q=0, ½, 1 is a norm defined by $$\|w_f^i\|_{0,\Omega_{i,f}} = \sum_{k \in \Omega_{i,f}} \left(1 - \delta_{0,w_{f,k}^i}\right),$$

$$\|w_f^i\|_{1/2,\Omega_{i,f}} = \sum_{k \in \Omega_{i,f}} \sqrt{|w_{f,k}^i|},$$

$$\|w_f^i\|_{1,\Omega_{i,f}} = \sum_{k \in \Omega_{i,f}} |w_{f,k}^i|$$

where $w_{f,k}^i$ is the $k^{th}$ element of the projector $w_f^i$, $\delta$ is the Kronecker symbol, and $\Omega_{i,f}$ is the set of indices corresponding to the penalisable elements of the projector $w_f^i$ at the PARAFAC iteration f.

Alternatively, an elementary minimisation step relating to a projector $w_f^i$ aims to minimise the penalised metrics $$\min_{w_{f,k}^i}\left(\left\|z_i^k - w_{f,k}^i\left(\left(w_f^M \otimes \ldots w_f^{i+1} \otimes w_f^{i-1} \otimes \ldots \otimes w_f^1\right)^T\right)\right\|^2 + \lambda_i g_q(w_{f,k}^i)\right),$$

k=1, . . . , $I_i$ where $z_i^k$ is the $k^{th}$ column vector of the matrix $\underline{XY}_{u(i)}$ of size $$I_i \times \prod_{\substack{n=1 \\ n \neq i}}^{N} I_n$$

obtained by deployment of the cross covariance tensor $\underline{XY}_u$ while taking the mode i as reference, $\otimes$ is the Kronecker product, $\lambda_i$ is a strictly positive coefficient, and the functions $g_q$, q=0, ½, 1 are defined by:

$g_0(w_{f,k}^i) = 1 - \delta_{0,w_{f,k}^i}$ if $k \in \Omega_{i,f}$ and $g_0(w_{f,k}^i) = 0$ if not $g_{1/2}(w_{f,k}^i) = \sqrt{|w_{f,k}^i|}$ if $k \in \Omega_{i,f}$ and $g_{1/2}(w_{f,k}^i) = 0$ if not $g_1(w_{f,k}^i) = |w_{f,k}^i|$ if $k \in \Omega_{i,f}$ and $g_1(w_{f,k}^i) = 0$ if not where $\Omega_{i,f}$ is the set of indices k corresponding to the penalisable elements $w_{f,k}^i$ of the projector $w_f^i$ at the PARAFAC iteration f.

In a particular embodiment, q=0 and the elements $w_{f,k}^i$ resulting from the minimisation are given by:

$(w_{f,k}^i)_{L0} = 0$ if $k \in \Omega_{i,f}$ and $|(w_{f,k}^i)_{LS}| \leq Th_{L0}^i$ $(w_{f,k}^i)_{L0} = (w_{f,k}^i)_{LS}$ if not where $(w_{f,k}^i)_{LS}$ represents the minimisation solution in the least squares sense:

$$(w_{f,k}^i)_{LS} = \frac{z_i^k\left(w_f^M \otimes \ldots w_f^{i+1} \otimes w_f^{i-1} \otimes \ldots \otimes w_f^1\right)}{\left\|w_f^M \otimes \ldots w_f^{i+1} \otimes w_f^{i-1} \otimes \ldots \otimes w_f^1\right\|^2}$$

and that the threshold $Th_{L0}^i$ is given by $$Th_{L0}^i = \frac{\sqrt{\lambda_i}}{\left\|w_f^M \otimes \ldots w_f^{i+1} \otimes w_f^{i-1} \otimes \ldots \otimes w_f^1\right\|}.$$

In a second particular embodiment, q=½ and the elements $w_{f,k}^i$ resulting from the minimisation are given by:

$(w_{f,k}^i)_{L0} = 0$ if $k \in \Omega_{i,f}$ and $|(w_{f,k}^i)_{LS}| \leq Th_{L0,5}^i$ $(w_{f,k}^i)_{L0} = \arg\min(h_{0,5}(0), h_{0,5}(B^i \cdot (w_{f,k}^i)_{LS}))$ if $k \in \Omega_{i,f}$ and $|(w_{f,k}^i)_{LS}| > Th_{L0,5}^i$ $(w_{f,k}^i)_{L0} = (w_{f,k}^i)_{LS}$ if not where $h_{0,5}(w_{f,k}^i) = \|z_1^k - w_{f,k}^i(w_f^3 \otimes w_f^2)^T\|^2 + \lambda_i \sqrt{|w_{f,k}^i|}$ and where $(w_{f,k}^i)_{LS}$ represents the minimisation solution in the least squares sense:

$$(w_{f,k}^i)_{LS} = \frac{z_i^k\left(w_f^M \otimes \ldots w_f^{i+1} \otimes w_f^{i-1} \otimes \ldots \otimes w_f^1\right)}{\left\|w_f^M \otimes \ldots w_f^{i+1} \otimes w_f^{i-1} \otimes \ldots \otimes w_f^1\right\|^2}$$

and the threshold $Th_{L0,5}^i$ is given by $$Th_{L0,5}^i = \frac{3}{4}\left(\frac{\lambda_i}{\left\|w_f^M \otimes \ldots w_f^{i+1} \otimes w_f^{i-1} \otimes \ldots \otimes w_f^1\right\|^2}\right)^{\frac{2}{3}}.$$

In a third particular embodiment, q=1 and the elements $w_{f,k}^i$ resulting from the minimisation are given by:

$(w_{f,k}^i)_{L1}=0$ if $k \in \Omega_{i,f}$ and $|(w_{f,k}^i)_{LS}| \leq Th_{L1}^i$ $(w_{f,k}^i)_{L1}=\text{sgn}((w_{f,k}^i)_{LS})(|(w_{f,k}^i)_{LS}|-Th_{L1}^i)$
  if $k \in \Omega_{i,f}$ and $|(w_{f,k}^i)_{LS}|>Th_{L1}^i$ $(w_{f,k}^i)_{L0}=(w_{f,k}^i)_{LS}$ if not where $(w_{f,k}^i)_{LS}$ represents the minimisation solution in the least squares sense:

$$(w_{f,k}^i)_{LS} = \frac{z_i^k(w_f^M \otimes \ldots w_f^{i+1} \otimes w_f^{i-1} \otimes \ldots \otimes w_f^1)}{\|w_f^M \otimes \ldots w_f^{i+1} \otimes w_f^{i-1} \otimes \ldots \otimes w_f^1\|^2}$$

and the threshold $Th_{L1}^i$ is given by $$Th_{L1}^i = \frac{\lambda_i}{\|w_f^M \otimes \ldots w_f^{i+1} \otimes w_f^{i-1} \otimes \ldots \otimes w_f^1\|}$$

Typically, said on-line calibration method may apply to electrophysiological signals constituted of ECoG signals.

BRIEF DESCRIPTION OF THE DRAWINGS

Other characteristics and advantages of the invention will become clear on reading the preferential embodiment of the invention, described with reference to the appended figures among which.

DETAILED DESCRIPTION OF PARTICULAR EMBODIMENTS

A direct neural interface with continuous decoding will be considered hereafter.

The electrophysiological signals coming from the different electrodes are sampled and grouped together by data blocks, each block corresponding to a sliding observation window of width $\Delta T$. Each observation window is defined by an observation time (epoch) at which the window in question starts.

The electrophysiological signals may be subjected to a pre-processing. This pre-processing may notably comprise a deletion of the average taken over the set of electrodes, then a time-frequency analysis is carried out on each of the observation windows.

The time-frequency analysis is based on a decomposition into wavelets, notably Morlet wavelets. Those skilled in the art will understand however that other types of time-frequency analysis could be envisaged by those skilled in the art.

These time-frequency analyses results may further be subjected to frequency smoothing or decimation.

Thus, with each observation window, or observation time t, is associated a tensor of order 3 of observation data, hence the generation of an input tensor of order 4: the first mode corresponds to the successive observation windows, the second mode corresponds to the space, in other words to the sensors, the third mode corresponds to the time within an observation window, in other words to the positions of the wavelets, and the fourth mode corresponds to the frequency, in other words to the number of frequency bands used for the decomposition into wavelets over an observation window.

More generally, the input tensor (or observation tensor) will be of order N, the first mode being in all cases that relative to the observation times (epochs). The input tensor (or observation tensor) is noted $\underline{X}$ and is of dimension $I_1 \times \ldots \times I_N$.

In the same way, the trajectory of the movement imagined, observed or made is described by an output tensor (or command tensor) of order M, noted $\underline{Y}$, of dimension $J_1 \times \ldots \times J_M$, of which the first mode corresponds to the successive times to which the commands will apply (as a general rule, this first mode also corresponds to the observation windows), the other modes corresponding to the commands of different effectors or to the other degrees of freedom of a multi-axis robot.

More specifically, the output tensor provides command data blocks, each of the blocks making it possible to generate command signals relative to the different effectors or degrees of freedom. Thus, it will be understood that the dimension of each data block could depend on the envisaged case of use and notably the number of degrees of freedom of the effector.

One will note hereafter $\underline{X}$, the observation tensor at the time t. This tensor is consequently of order N and of dimension $I_1 \times \ldots \times I_N$. It takes its values in a space $\underline{X} \subset \square^{I_1 \times \ldots \times I_N}$ where $\square$ is the set of real values. Similarly, one will note $\underline{Y}$, the command tensor at the time t. This output tensor is of order M and of dimension $J_1 \times \ldots \times J_M$. It takes its values in a space $\underline{Y} \subset \square \underline{X}_u \in \square^{J_1 \times \ldots \times J_M}$.

The calibration or, in an equivalent manner, the mechanism for updating the predictive model according to the REW-NPLS (Recursive Exponentially Weighted N-way Partial Least Squares) algorithm is recalled hereafter.

If one notes $\{\underline{X}_u, \underline{Y}_u\}$ the calibration data blocks (or training data sets) during the iteration u the basic idea of the REW-NPLS algorithm is to update the predictive model from the covariance and cross covariance tensors obtained at the preceding calibration step, respectively noted $\underline{XX}_{u-1}$ and $\underline{XY}_{u-1}$. These two tensors make it possible to obtain a condensed representation of the predictive model at the preceding step, without there being a need to store the history of preceding calibration data blocks: $\{\underline{X}_1, \underline{Y}_1\}, \{\underline{X}_2, \underline{Y}_2\}, \ldots \{\underline{X}_{u-1}, \underline{Y}_{u-1}\}$.

More specifically, the covariance and cross covariance tensors are updated by means of recurrence relationships:

$\underline{XX}_u = \gamma \underline{XX}_{u-1} + \underline{X}_u \times_1 \underline{X}_u$ \hfill (1-1)

$\underline{XY}_u = \gamma \underline{XY}_{u-1} + \underline{X}_u \times_1 \underline{Y}_u$ \hfill (1-2)

where $\times_1$ designates the tensor product of mode 1 and $\gamma$ is a forgetting coefficient with $0 < \gamma < 1$.

One thus understands that a current calibration period, carried out during the iteration u takes account of a preceding calibration period carried out during the iteration u−1 and the tensors of the observation data of the current calibration period, the history being weighted by the forgetting coefficient $\gamma$ with $0<\gamma<1$.

This operation of updating the covariance tensors is carried out in an iterative manner over the calibration periods.

Figure 1A:
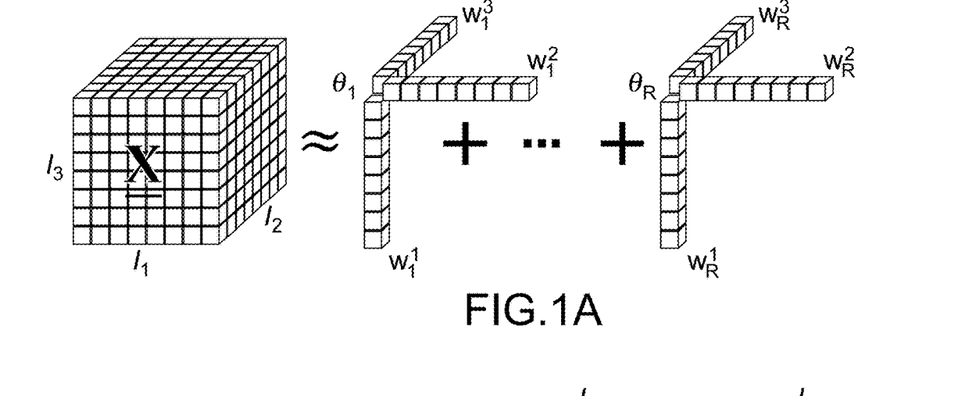
FIG. 1A schematically represents the decomposition of a tensor by parallel factorial analysis (PARAFAC)
Figure 1B:
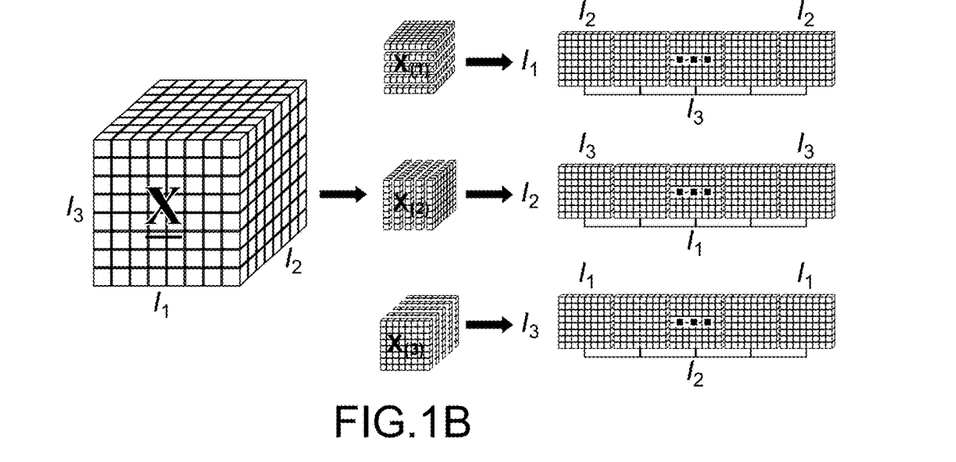
FIG. 1B schematically represents the development of a tensor with respect to a mode.

For each update, the predictive model is next obtained in an iterative manner by means of a PARAFAC decomposition (generalisation to the tensorial case of a decomposition into singular values) of the cross covariance tensor, $\underline{XY}_u$. It will be recalled that, generally speaking, a PARAFAC decomposition of a tensor $\underline{Z}$ of order M, i.e. $\underline{Z} \in \square^{I_1 \times I_2 \times \cdots \times I_M}$ makes it possible to represent this tensor in the form of a linear combination of external products of vectors (tensors of order 1) to a nearest residual tensor:

$$\underline{Z} = \sum_{r=1}^{R} \theta_r w_r^1 \circ w_r^2 \circ \ldots \circ w_r^M + \underline{E} \quad (2)$$

with $\|w_r^m\|=1$, $m=1, \ldots, M$ where $\circ$ is the external product and $\underline{E}$ is a residual tensor and r is the index of the PARAFAC iteration and R is a given integer. A PARAFAC decomposition of a tensor $\underline{Z}$ has been represented schematically in FIG. 1A.

In the case of a REW-NPLS calibration step, each PARAFAC iteration only relates to an elementary decomposition, that is to say R=1. It makes it possible to extract from the tensor $\underline{XY}_u$ a set of projection vectors, also designated projectors, $w_f^1, \ldots, w_f^M$, of respective $I_1, I_2, \ldots, I_M$ where the iteration number f gives the dimension of a latent variables space onto which the input tensor $\underline{X}_u$ is projected.

In order to simplify the presentation and without prejudice of generalisation to a tensor of any order, we will assume hereafter that the order of the tensor $\underline{XY}_u$ is equal to 3 (M=3), that is to say $\underline{XY}_u \in \square^{I_1 \times I_2 \times I_3}$ with $\|\underline{XY}_u\|=1$ For example, the first mode corresponds to the epoch, the second to the frequency and the third to the space (that is to say to the electrodes).

At the iteration f of the PARAFAC decomposition, one searches for the projection vectors $w_f^1$, $w_f^2$, $w_f^3$ which verify:

$$\min_{\underline{XY}_u} \|\underline{XY}_u - \underline{\hat{XY}}_u\|^2 \text{ with}$$

$$\underline{\hat{XY}}_u = \theta_f w_f^1 \circ w_f^2 \circ w_f^3 \text{ and}$$

$$\|w_f^1\| = \|w_f^2\| = \|w_f^3\| = 1$$

This minimisation problem may be resolved by an alternating least squares method in which one carries out sequentially a minimisation for each of the vectors of the decomposition, i.e.:

$$\min_{w_f^1} \|\underline{XY}_{u(1)} - w_f^1 (w_f^3 \otimes w_f^2)^T\|^2 \quad (4-1)$$

$$\min_{w_f^2} \|\underline{XY}_{u(2)} - w_f^2 (w_f^3 \otimes w_f^1)^T\|^2 \quad (4-2)$$

$$\min_{w_f^3} \|\underline{XY}_{u(3)} - w_f^3 (w_f^2 \otimes w_f^1)^T\|^2 \quad (4-3)$$

where $\otimes$ is the Kronecker product and $\underline{Z}_{(n)}$ is a matrix obtained by deployment of the tensor $\underline{Z}$ while taking the mode n as reference mode (tensor unfolding or flattening along mode n). For example, the matrix $\underline{Z}_{(1)}$ is defined by $(z_1^1 | \ldots | z_1^{I_1}) \in \square^{I_1 \times I_2 I_3}$ where the $Z_1^j$ are the columns of the matrix $\underline{Z}_{(1)}$.

The minimisation operations (4-1), (4-2) and (4-3) are repeated up to convergence. the minimisation solutions in the least squares (LS) sense for each of these operations are given by the projectors:

$$w_f^1 = \frac{\underline{XY}_{u(1)}(w_f^3 \otimes w_f^2)}{\|w_f^3 \otimes w_f^2\|^2} \quad (5-1)$$

$$w_f^2 = \frac{\underline{XY}_{u(2)}(w_f^3 \otimes w_f^1)}{\|w_f^3 \otimes w_f^1\|^2} \quad (5-2)$$

$$w_f^3 = \frac{\underline{XY}_{u(3)}(w_f^2 \otimes w_f^1)}{\|w_f^2 \otimes w_f^1\|^2} \quad (5-3)$$

Each iteration f of the PARAFAC decomposition provides a plurality M of projectors $w_f^1, \ldots, w_f^M$ and a prediction coefficients tensor, or predictive model of the direct neural interface, defined by a prediction coefficients tensor $\underline{B}_N^f \in \square^{(I_1 \times \ldots \times I_N) \times (J_1 \times \ldots \times J_M)}$ and a bias tensor $\underline{\beta}_u^f \in \square^{(J_1 \times \ldots \times J_M)}$, making it possible to predict the command tensor from the observation tensor. One thus obtains a plurality of models, $\underline{B}_u^f$, f=1, ..., F corresponding to different successive dimensions of the latent variables space.

One next determines, at the following calibration step, u+1, among $\underline{B}_u^f$, f=1, ..., F, the predictive model $\underline{B}_u^{f*}$ corresponding to the smallest prediction error where one has noted f* the index f corresponding to this smallest prediction error. This determination of the predictive model at the following calibration step is designated in the literature under the term recursive validation.

Figure 1C:
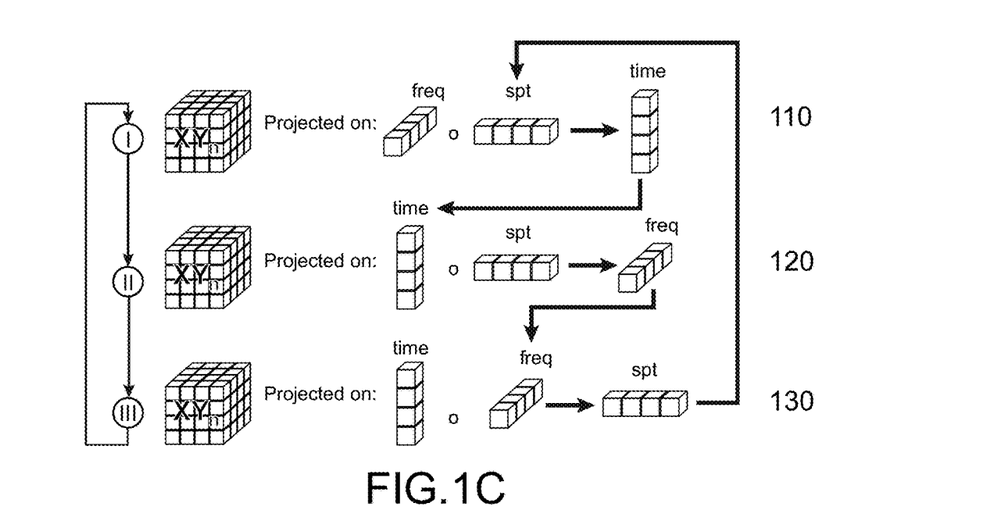
FIG. 1C schematically represents a decomposition using an alternating least squares (ALS) method.

FIG. 1C schematically represents a decomposition using an alternating least squares (ALS) method.

The decomposition by alternating least squares has been illustrated for a REW-NPLS calibration step and a PARAFAC iteration f.

At step 110, one estimates the vector $w_f^1$ (corresponding to the epoch mode) from the matrix $\underline{XY}_{u(1)}$ and the current vectors $w_f^2$ and $w_f^3$. This operation may be considered as a projection of the column vectors of the matrix $\underline{XY}_{u(1)}$ onto the tensorial space generated by the modes 2 and 3.

At step 120, one estimates the vector $w_f^2$ (corresponding to the frequency mode) from the matrix $\underline{XY}_{u(2)}$ and the current vectors $w_f^1$ and $w_f^3$. This operation may be considered as a projection of the column vectors of the matrix $\underline{XY}_{u(2)}$ onto the tensorial space generated by the modes 1 and 3.

At step 130, one estimates the vector $w_f^3$ (corresponding to the spatial mode) from the matrix $\underline{XY}_{u(3)}$ and the current vectors $w_f^1$ and $w_f^2$. This operation may be considered as a projection of the column vectors of the matrix $\underline{XY}_{u(3)}$ onto the tensorial space generated by the modes 1 and 2.

Steps 110, 120, 130 are iterated until a convergence criterion is met, for example when the sum of the deviations between the vectors $w_f^j$ of two successive ALS iterations is less than a predetermined threshold value.

The basic idea of the present invention is to carry out a penalisation by section at each iteration of the PARAFAC algorithm, a penalisation by section resulting in an elimination of elements relative to an index value in the tensor of the prediction model. The elements not being subjected to a penalisation during an iteration f are no longer penalisable for the following iterations, f+1, f+2, ..., F. On the other hand, the elements penalised during an iteration are taken into account during the PARAFAC decomposition of the following iteration. One thus promotes a blockwise sparsity of non-zero elements in the tensor of the prediction model, which considerably simplifies the calculation of the command.

More specifically, during an iteration f of the PARAFAC decomposition, the minimisation of the quadratic deviations according to (4-1), (4-2) and (4-3) in the alternating least squares method is replaced by a minimisation taking into account a penalisation term favouring this sparsity, namely:

$$\min_{\tilde{w}_f^1}\left(\|\underline{XY}_{u(1)} - \tilde{w}_f^1(w_f^3 \otimes w_f^2)^T\|^2 + \lambda_1\|\tilde{w}_f^1\|_{q,\Omega_{1,f}}\right) \quad (6\text{-}1)$$

$$\min_{\tilde{w}_f^2}\left(\|\underline{XY}_{u(2)} - \tilde{w}_f^2(w_f^3 \otimes w_f^1)^T\|^2 + \lambda_2\|\tilde{w}_f^2\|_{q,\Omega_{2,f}}\right) \quad (6\text{-}2)$$

$$\min_{\tilde{w}_f^3}\left(\|\underline{XY}_{u(3)} - \tilde{w}_f^3(w_f^2 \otimes w_f^1)^T\|^2 + \lambda_3\|\tilde{w}_f^3\|_{q,\Omega_{3,f}}\right) \quad (6\text{-}3)$$

where $\tilde{w}_f^1$, $\tilde{w}_f^2$ and $\tilde{w}_f^3$ are non-normalised projectors and $$w_f^1 = \frac{\tilde{w}_f^1}{\|\tilde{w}_f^1\|},$$

$$w_f^2 = \frac{\tilde{w}_f^2}{\|\tilde{w}_f^2\|},$$

$$w_f^3 = \frac{\tilde{w}_f^3}{\|\tilde{w}_f^3\|}$$

are the corresponding normalised projectors and $\lambda_1$, $\lambda_2$, $\lambda_3$ are coefficients that are strictly positive and less than 1. It will be noted that due to the presence of penalisation terms in the expressions (6-1), (6-2) and (6-3), the minimisation can no longer be carried out on normalised projection vectors as in the classic ALS method. The norms $\|w_f^i\|_{q,\Omega_i}$ q=0, ½, 1 are defined by:

$$\|w_f^i\|_{0,\Omega_{i,f}} = \sum_{k\in\Omega_{i,f}}\left(1 - \delta_{0,w_{f,k}^i}\right) \quad (7\text{-}1)$$

$$\|w_f^i\|_{1/2,\Omega_{i,f}} = \sum_{k\in\Omega_{i,f}}\sqrt{|w_{f,k}^i|} \quad (7\text{-}2)$$

$$\|w_f^i\|_{1,\Omega_{i,f}} = \sum_{k\in\Omega_{i,f}}|w_{f,k}^i| \quad (7\text{-}3)$$

where $w_{f,k}^i$ is the $k^{th}$ element of the projection vector $w_f^i$, $\delta$ is the Kronecker symbol, and $\Omega_{i,f}$ is the set of indices corresponding to the penalisable elements, it being understood that $\Omega_{i,f+1} \cap \Omega_{i,f}$ since the non-penalised elements of a projector at an iteration f are not penalisable at the iteration f+1.

It will notably be understood that the norm of the expression (7-1) gives the sum of the non-zero elements of which the indices belong to $\Omega_{i,f}$. Thus for example, in this case, the penalisation will be all the greater when the number of elements of which the indices belong to $\Omega_{i,f}$ is higher.

In order to simplify the minimisation calculation in the expressions (6-1), (6-2), (6-3), one could advantageously operate element by element, namely:

$$\min_{w_{f,k}^1}\left(\|z_1^k - w_{f,k}^1(w_f^3 \otimes w_f^2)^T\|^2 + \lambda_1 g_q(w_{f,k}^1)\right), k = 1, \ldots, I_1 \quad (8\text{-}1)$$

$$\min_{w_{f,k}^2}\left(\|z_2^k - w_{f,k}^2(w_f^3 \otimes w_f^1)^T\|^2 + \lambda_2 g_q(w_{f,k}^2)\right), k = 1, \ldots, I_2 \quad (8\text{-}2)$$

$$\min_{w_{f,k}^3}\left(\|z_3^k - w_{f,k}^3(w_f^2 \otimes w_f^1)^T\|^2 + \lambda_3 g_q(w_{f,k}^3)\right), k = 1, \ldots, I_3 \quad (8\text{-}3)$$

where the vectors $z_1^k$, $z_2^k$, $z_3^k$ are the $k^{th}$ column vectors of the matrices $\underline{XY}_{u(1)}$, $\underline{XY}_{u(2)}$, $\underline{XY}_{u(3)}$ obtained by deployment of the cross covariance tensor $\underline{XY}_u$ according to modes 1, 2 and 3, respectively.

The functions $g_q$, q=0, ½, 1 apply to scalar values and are defined by:

$$g_0(w_{f,k}^i) = 1 - \delta_{0,w_{f,k}^i} \text{ if } k \in \Omega_{i,f} \text{ and } g_0(w_{f,k}^i) = 0 \text{ if not} \quad (9\text{-}1)$$

$$g_{1/2}(w_{f,k}^i) = \sqrt{|w_{f,k}^i|} \text{ if } k \in \Omega_{i,f} \text{ and } g_{1/2}(w_{f,k}^i) = 0 \text{ if not} \quad (9\text{-}2)$$

$$g_1(w_{f,k}^i) = |w_{f,k}^i| \text{ if } k \in \Omega_{i,f} \text{ and } g_1(w_{f,k}^i) = 0 \text{ if not} \quad (9\text{-}3)$$

It may be shown that the result of the penalised minimisation operation according to (8-1), (8-2), (8-3) for the norm $L_0$ (that is to say q=0) gives:

$$(w_{f,k}^i)_{L0} = 0 \text{ if } k \in \Omega_{i,f} \text{ and } |(w_{f,k}^i)_{LS}| \leq Th_{L0}^i \quad (10\text{-}1)$$

$$(w_{f,k}^i)_{L0} = (w_{f,k}^i)_{LS} \text{ if not} \quad (10\text{-}2)$$

where $(w_{f,k}^i)_{LS}$ represents the minimisation solution in the least squares sense (5-1), (5-2), (5-3), that is to say:

$$(w_{f,k}^1)_{LS} = \frac{z_1^k(w_f^3 \otimes w_f^2)}{\|w_f^3 \otimes w_f^2\|^2} \quad (11\text{-}1)$$

$$(w_{f,k}^2)_{LS} = \frac{z_2^k(w_f^3 \otimes w_f^1)}{\|w_f^3 \otimes w_f^1\|^2} \quad (11\text{-}2)$$

$$(w_{f,k}^3)_{LS} = \frac{z_3^k(w_f^2 \otimes w_f^1)}{\|w_f^2 \otimes w_f^1\|^2} \quad (11\text{-}3)$$

and the thresholds $Th_{L0}^i$, i=1, 2, 3 are given by:

$$Th_{L0}^1 = \frac{\sqrt{\lambda_1}}{\|w_f^3 \otimes w_f^2\|} \quad (12\text{-}1)$$

$$Th_{L0}^2 = \frac{\sqrt{\lambda_2}}{\|w_f^3 \otimes w_f^1\|} \quad (12\text{-}2)$$

$$Th_{L0}^3 = \frac{\sqrt{\lambda_3}}{\|w_f^2 \otimes w_f^1\|} \quad (12\text{-}3)$$

The penalised minimisation operation consequently comes down to carrying out a thresholding on the elements of the projectors obtained at each step of the ALS method.

Similarly, it may be shown that the penalised minimisation operation according to (8-1), (8-2), (8-3) for the norm $L_{1/2}$ (that is to say q=½) has for solution:

$$(w_{f,k}^i)_{L0} = 0 \text{ if } k \in \Omega_{i,f} \text{ and } |(w_{f,k}^i)_{LS}| \leq Th_{L0,5}^i \quad (13\text{-}1)$$

$$(w_{f,k}^i)_{L0} = \arg\min(h_{0,5}(0), h_{0,5}(B^i \cdot (w_{f,k}^i)_{LS})) \text{ if } k \in \Omega_{i,f}$$
$$\text{and } |(w_{f,k}^i)_{LS}| > Th_{L0,5}^i \quad (13\text{-}2)$$

$$(w_{f,k}^i)_{L0} = (w_{f,k}^i)_{LS} \text{ if not} \quad (13\text{-}3)$$

where $h_{0,5}(w_{f,k}{}^i) = \|z_1{}^k - w_{f,k}{}^i(w_f{}^3 \otimes w_f{}^2)^T\|^2 + \lambda_i \sqrt{|w_{f,k}{}^i|}$ and the thresholds $Th_{L0,5}{}^i$, i=1, 2, 3 are given by:

$$Th_{L0,5}^1 = \frac{3}{4}\left(\frac{\lambda_1}{\|w_f^3 \otimes w_f^2\|^2}\right)^{\frac{2}{3}} \quad (14\text{-}1)$$

$$Th_{L0,5}^2 = \frac{3}{4}\left(\frac{\lambda_2}{\|w_f^3 \otimes w_f^1\|^2}\right)^{\frac{2}{3}} \quad (14\text{-}2)$$

$$Th_{L0,5}^3 = \frac{3}{4}\left(\frac{\lambda_3}{\|w_f^2 \otimes w_f^1\|^2}\right)^{\frac{2}{3}} \quad (14\text{-}3)$$

The coefficients $B^i$, i=1, 2, 3 are defined as the respective solutions of the cubics $x(1-x)^2 = C_i$, i=1, 2, 3, with:

$$C^1 = \frac{\lambda_1^2}{16\|w_f^3 \otimes w_f^2\|^4((w_{f,k}^1)_{LS})^3} \quad (15\text{-}1)$$

$$C^2 = \frac{\lambda_2^2}{16\|w_f^3 \otimes w_f^1\|^4((w_{f,k}^2)_{LS})^3} \quad (15\text{-}2)$$

$$C^3 = \frac{\lambda_3^2}{16\|w_f^2 \otimes w_f^1\|^4((w_{f,k}^3)_{LS})^3} \quad (15\text{-}3)$$

Finally, similarly, it may be shown that the penalised minimisation operation according to (8-1), (8-2), (8-3) for the norm $L_1$ (that is to say q=1) has for solution:

$(w_{f,k}{}^i)_{L1} = 0$ if $k \in \Omega_{i,f}$ and $|(w_{f,k}{}^i)_{LS}| \leq Th_{L1}{}^i$ (16-1)

$(w_{f,k}{}^i)_{L1} = \text{sgn}((w_{f,k}{}^i)_{LS})(|(w_{f,k}{}^i)_{LS}| - Th_{L1}{}^i)$ if $k \in \Omega_{i,f}$ and $|(w_{f,k}{}^i)_{LS}| > Th_{L1}{}^i$ (16-2)

$(w_{f,k}{}^i)_{L0} = (w_{f,k}{}^i)_{LS}$ if not (16-3)

where the thresholds $Th_{L1}{}^i$, i=1, 2, 3 are given by:

$$Th_{L1}^1 = \frac{\lambda_1}{\|w_f^3 \otimes w_f^2\|} \quad (17\text{-}1)$$

$$Th_{L1}^2 = \frac{\lambda_2}{\|w_f^3 \otimes w_f^1\|} \quad (17\text{-}2)$$

$$Th_{L1}^3 = \frac{\lambda_3}{\|w_f^2 \otimes w_f^1\|} \quad (17\text{-}3)$$

It will be understood that, whatever the norm used, the penalised minimisation is advantageously reduced to a simple thresholding of the elements of a projector at each step of the ALS method. This penalised minimisation makes it possible to promote blockwise sparsity of non-zero coefficients in the predictive model and consequently to simplify the calculation. It is important to note that this may be carried out on-line with the aim of carrying out an incremental calibration of the predictive model.

Figure 2:
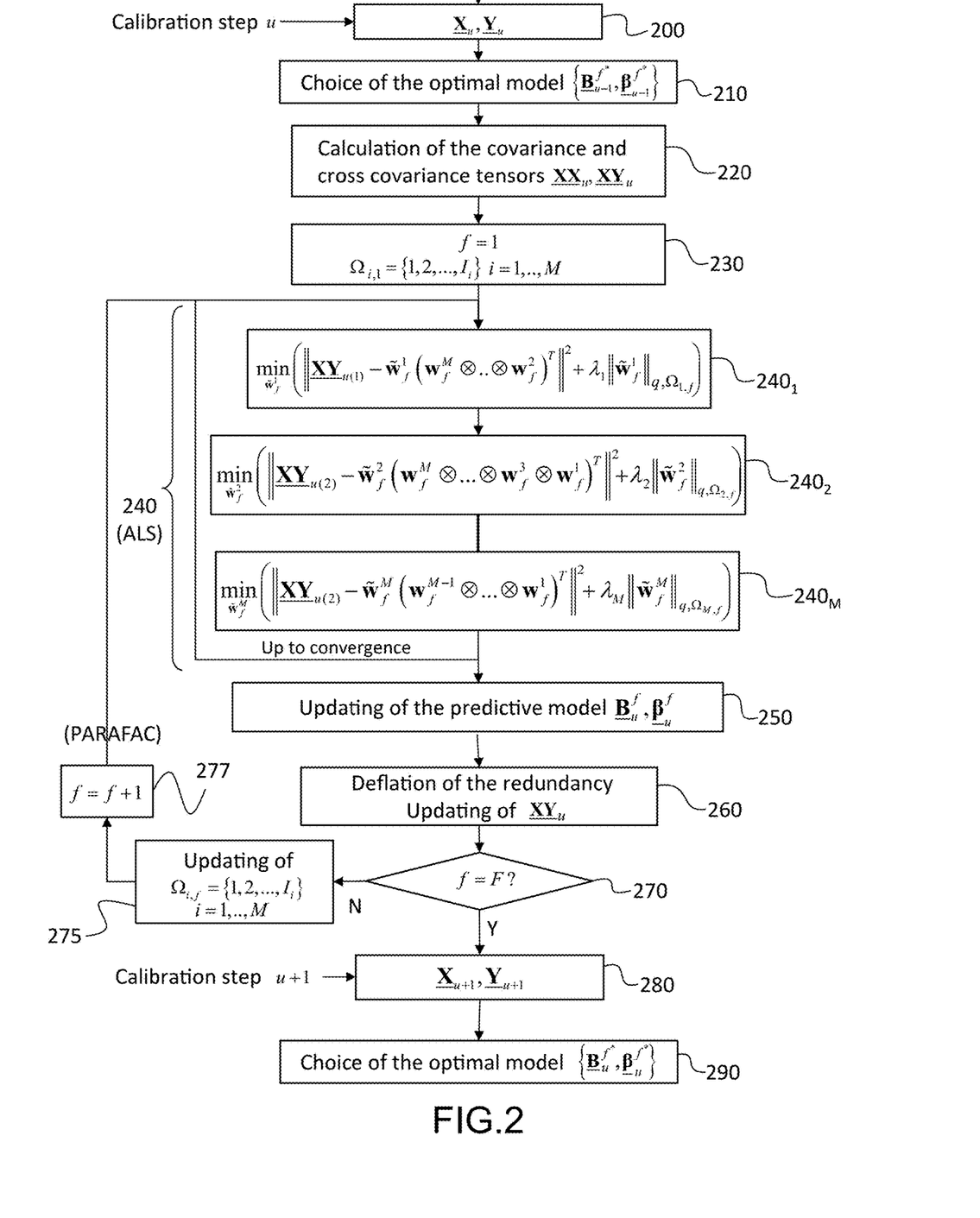
FIG. 2 schematically represents the flowchart of a recursive method for calibrating a direct neural interface with penalised multivariate regression, according to an embodiment of the present invention.

FIG. 2 schematically represents the flow chart of a recursive method for calibrating a direct neural interface with penalised multivariate regression, according to an embodiment of the present invention.

At step 200, one takes into account new input and output calibration data, respectively in the form of an input tensor $\underline{X}_\mu$ and an output tensor $\underline{Y}_\mu$. The input calibration data result from the measurement of electrophysiological signals. The output calibration data result for example from the measurement of kinematic parameters of the trajectory or command signals of effectors. The input and output tensors may be if appropriate subjected to a pre-processing aiming to centre and normalise them, in a manner known per se.

At step 210, one determines among the set of predictive models $\underline{B}_{\mu-1}{}^f$, $\underline{\beta}_{\mu-1}{}^f$, f=1, ..., F obtained at the preceding step, the predictive model $\{\underline{B}_{\mu-1}{}^{f*}, \underline{\beta}_{\mu-1}{}^{f*}\}$ corresponding to the lowest prediction error. This model is used to calculate the command tensor (output tensor) from the observation tensor (input tensor).

At step 220, one updates the covariance $\underline{XX}_\mu$ and cross covariance, $\underline{XY}_\mu$, tensors according to the relationships (1-1) and (1-2), while taking account of the forgetting factor.

One next enters into a first NPLS iterative loop, in which one iterates on the dimension f of the latent variables space, with f=1, ..., F where F is a maximum dimension. This iterative loop makes it possible to generate successively a plurality of predictive models of the direct neural interface, each predictive model being defined by a prediction coefficients tensor $\underline{B}_\mu{}^f \in \square^{(I_1 \times \ldots \times I_M) \times (J_1 \times \ldots \times J_M)}$ and a bias tensor $\underline{\beta}_\mu{}^f \in \square^{(J_1 \times \ldots \times J_M)}$.

At step 230, one initialises f with f=1 and the sets $\Omega_{i,1}$, i=1, ..., M with $\Omega_{i,1} = \{1, 2, \ldots, I_i\}$ for i=1, ..., M.

For each value of f, one carries out a PARAFAC decomposition of the cross covariance tensor using an alternating least squares method. Unlike a conventional PARAFAC decomposition (cf. expressions (4-1), (4-2), (4-3)) used in the REW-NPLS method, a PARAFAC decomposition regularised by means of a penalised metric is used here, the penalisation term aiming to promote blockwise sparsity of non-zero coefficients within the tensor representative of the predictive model.

More specifically, in 240, for each value of f, one searches for the M-uplet of projectors $w_f{}^i$, i=1, ..., M of respective dimensions $I_1, I_2, \ldots, I_M$ making it possible to minimise said penalised metric, as expressed in (6-1), (6-2), (6-3) in the case M=3. This minimisation takes place sequentially by ALS, projector by projector in $240_1, \ldots, 240_M$, the other projectors being considered as constant.

Advantageously, at each of these steps, the minimisation relates to the elements of the projector in question, as described in relation with the expressions (8-1) to (8-3) and (9-1) to (9-3).

More specifically, at each step, the elements of the projector making it possible to minimise the penalised metric are obtained by means of a thresholding of the elements of the projector minimising the non-penalised metric, as described in relation with the expressions (10-1), (10-2); (13-1) to (13-3); (16-1) to (16-3).

It is important to note that at each iteration f, only the penalisable elements are taken into account for the minimisation of the metric. To this end, one eliminates from the set of penalisable indices $\Omega_{i,f}$, the indices $k \in \Omega_{i,f}$ for which the elements $w_{f,k}{}^i$ have not been penalised at the iteration f, to generate the set of penalisable indices relative to the following iteration, $\Omega_{i,f+1}$.

The tensor of the predictive model, $\underline{B}_\mu{}^f$, is obtained from the projectors $w_\varphi{}^i$, i=, ..., M, $\varphi = 1, \ldots,$ f as in the conventional REW-NPLS regression method. Details of the calculation of $\underline{B}_\mu{}^f$ from the projectors in question will be found in appendix A of the article of A. Eliseyev et al. published in 2017, cited in the introduction part. The elements of the predictive model $\underline{B}_\mu{}^f$ corresponding to the indices for which the elements $w_{f,k}{}^i$ have been penalised, are zeroed in 250.

After each iteration f, one eliminates in 260, from $\underline{XX}_\mu$ and $\underline{XY}_\mu$ the redundant information already taken into account in the regression on the latent variables space, at the preceding iterations 1, ..., f. The cross-covariance tensor $\underline{XY}_u$ in which this redundancy has been eliminated is used for the new PARAFAC decomposition iteration. Step 260 is known by the name deflation in the NPLS regression.

At the end of the F iterations, in 270, one consequently has available F predictive models, $\underline{B}_{u-1}^f, \underline{\beta}_{u-1}^f$, f=1, ..., F.

After the acquisition of new input calibration data, $\underline{X}_{u+1}$ and output calibration data, $\underline{Y}_{u+1}$ blocks at the following calibration step, 280, one determines in 290, the optimal predictive model, $\{\underline{B}_u^{f*}, \underline{\beta}_u^{f*}\}$. This predictive model is used to calculate the command tensor from the observation tensor, up to the following calibration step, u+2.

Figure 3:
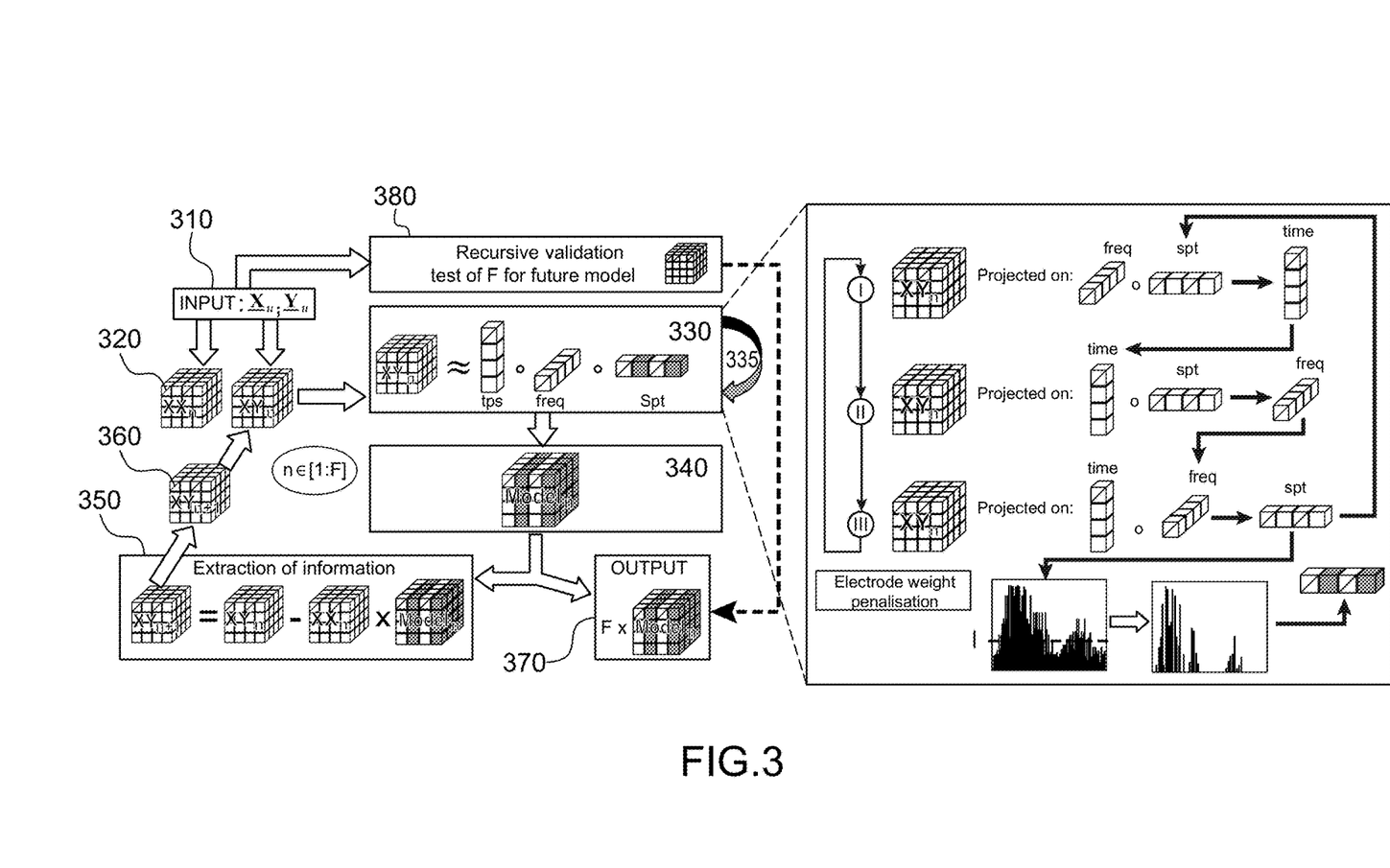
FIG. 3 schematically represents the mechanism for updating the predictive model in the calibration method of FIG. 2.

FIG. 3 schematically represents the mechanism for updating the predictive model in the calibration method of FIG. 2.

In 310 is represented the taking into account of a new input calibration data block, represented by the tensor $\underline{X}_u$ and a new output calibration block, represented by the tensor $\underline{Y}_u$.

The covariance $\underline{XX}_u$ and cross covariance, $\underline{XY}_u$, tensors are deduced therefrom in 320.

For each value of f, a PARAFAC decomposition of the cross-covariance tensor is carried out using an alternating least squares (ALS) method in 330, each step of the PARAFAC decomposition relating to a projector, this decomposition being regularised by means of a penalisation term relating to this projector. The regularisation results in a thresholding of certain elements of the projector obtained by the conventional least squares method, that is to say non-penalised.

At each PARAFAC iteration represented by the loop 335, one deduces therefrom a predictive model $\{\underline{B}_u^f, \underline{\beta}_u^f\}$ in 340.

For each predictive model, one eliminates in 350 the redundant information in the cross-covariance tensor (deflation) and one carries out a new PARAFAC iteration on the covariance tensor $\underline{XX}_u$ and the new cross covariance tensor $\underline{XY}_u$ (noted $XY_{n+1}$ in the figure) deflated of said redundancy, 360.

The recursive validation loop is represented in 380. It makes it possible to determine among the predictive models $\{\underline{B}_u^f, \underline{\beta}_u^f\}$, f=1, ..., F, obtained at the preceding calibration step, that which minimises the prediction error on the new input, $\underline{X}_{u+1}$, and output, $\underline{Y}_{u+1}$ calibration data blocks.

The invention claimed is:

1. Method for calibrating on-line a direct neural interface intended to receive a plurality of electrophysiological signals during a plurality of observation windows associated with observation times, to form an input tensor and to deduce therefrom, by means of a predictive model, an output tensor providing command signals intended to command one or more effectors, said calibration is carried out during a plurality of calibration steps, calibration step u being carried out from input calibration data, represented by an input calibration tensor, $\underline{X}_u \in \square^{(I_1 \times \cdots \times I_N)}$, and output calibration data represented by an output calibration tensor $\underline{Y}_u \in \square^{(J_1 \times \cdots \times J_M)}$, said calibration step implementing a REW-NPLS regression comprising:

the calculation (220) of a covariance tensor $\underline{XX}_u$ from a covariance tensor $\underline{XX}_{u-1}$ obtained during a preceding calibration step and the tensor $\underline{X}_u$, as well as the calculation of a cross covariance tensor $\underline{XY}_u$ from a cross covariance tensor $\underline{XY}_{u-1}$ obtained during said preceding calibration step and the tensors $\underline{X}_u$ and $\underline{Y}_u$;

a PARAFAC iterative decomposition of the cross covariance tensor $\underline{XY}_u$, each PARAFAC iteration being associated with a dimension f of the latent variables space on which said regression is carried out, each iteration providing a plurality of projectors $w_f^i$, i=1, ..., M of respective sizes $I_1, I_2, \ldots I_M$ and a predictive model defined by a prediction coefficients tensor $\underline{B}_u^f \in \square^{(I_1 \times \cdots \times I_M) \times (J_1 \times \cdots \times J_M)}$ and a bias tensor $\underline{\beta}_u^f \in \square^{(J_1 \times \cdots \times J_M)}$;

characterised in that each PARAFAC iteration comprises a sequence of M elementary steps (240$_1$, 240$_1$, ... 240$_M$) of minimisation of a metric according to the alternating least squares method, each elementary minimisation step relating to a projector and considering the others as constant, said metric comprising a penalisation term that is a function of the norm of this projector, the elements of this projector not being subjected to a penalisation during a PARAFAC iteration f not being penalisable during following PARAFAC iterations.

2. Method for calibrating on-line a direct neural interface according to claim 1, characterised in that an elementary minimisation step relating to a projector $w_f^i$ aims to minimise the penalised metric $$\min_{\tilde{w}_f^i}\left(\left\|\underline{XY}_{u(i)} - \tilde{w}_f^i\left(w_f^M \otimes \ldots w_f^{i+1} \otimes w_f^{i-1} \otimes \ldots \otimes w_f^1\right)^T\right\|^2 + \lambda_i \|\tilde{w}_f^i\|_{q,\Omega_{i,f}}\right)$$

where $\tilde{w}_f^i$ is a non-normalised projector and $$w_f^m = \frac{\tilde{w}_f^m}{\|\tilde{w}_f^m\|},$$

m=1, ... M; m≠i are normalised projectors, $\underline{XY}_{u(i)}$ is a matrix of size $$I_i \times \prod_{\substack{n=1 \\ n \neq i}}^{N} I_n$$

obtained by deployment of the cross covariance tensor $\underline{XY}_u$ while taking the mode i as reference, ⊗ is the Kronecker product, $\lambda_i$ is a strictly positive coefficient, $\|w\|_{q,\Omega_{i,f}}$, q=0, ½, 1 is a norm defined by $$\|w_f^i\|_{0,\Omega_{i,f}} = \sum_{k \in \Omega_{i,f}}\left(1 - \delta_{0,w_{f,k}^i}\right),$$

$$\|w_f^i\|_{1/2,\Omega_{i,f}} = \sum_{k \in \Omega_{i,f}} \sqrt{|w_{f,k}^i|}, \quad \|w_f^i\|_{1,\Omega_{i,f}} = \sum_{k \in \Omega_{i,f}} |w_{f,k}^i|$$

where $w_{f,k}^i$ is the $k^{th}$ element of the projector $w_f^i$, δ is the Kronecker symbol, and $\Omega_{i,f}$ is the set of indices corresponding to the penalisable elements of the projector $w_f^i$ at the PARAFAC iteration f.

3. Method for calibrating on-line a direct neural interface according to claim 1, characterised in that an elementary minimisation step relating to a projector $w_f^i$ aims to minimise the penalised metrics $$\min_{w_{f,k}^i}\left(\left\|z_i^k - w_{f,k}^i\left(\left(w_f^M \otimes \ldots w_f^{i+1} \otimes w_f^{i-1} \otimes \ldots \otimes w_f^1\right)^T\right)^T\right\|^2 + \lambda_i g_q(w_{f,k}^i)\right),$$

$k=1, \ldots, I_i$ where $z_i^k$ is the $k^{th}$ column vector of the matrix $\underline{XY}_{u(i)}$ of size $$I_i \times \prod_{\substack{n=1 \\ n \neq i}}^{N} I_n$$

obtained by deployment of the cross covariance tensor $\underline{XY}_u$ while taking the mode i as reference, $\otimes$ is the Kronecker product, $\lambda_i$ is a strictly positive coefficient, and the functions $g_q$, $q=0, \frac{1}{2}, 1$ are defined by:

$g_0(w_{f,k}^i) = 1 - \delta_{0,w_{f,k}^i}$ if $k \in \Omega_{i,f}$ and $g_0(w_{f,k}^i) = 0$ if not $g_{1/2}(w_{f,k}^i) = \sqrt{|w_{f,k}^i|}$ if $k \in \Omega_{i,f}$ and $g_{1/2}(w_{f,k}^i) = 0$ if not $g_1(w_{f,k}^i) = |w_{f,k}^i|$ if $k \in \Omega_{i,f}$ and $g_1(w_{f,k}^i) = 0$ if not where $\Omega_{i,f}$ is the set of indices k corresponding to the penalisable elements $w_{f,k}^i$ of the projector $w_f^i$ at the PARAFAC iteration f.

4. Method for calibrating on-line a direct neural interface according to claim 3, characterised in that q=0 and that the elements $w_{f,k}^i$ resulting from the minimisation are given by:

$(w_{f,k}^i)_{L0} = 0$ if $k \in \Omega_{i,f}$ and $|(w_{f,k}^i)_{LS}| \leq Th_{L0}^i$ $(w_{f,k}^i)_{L0} = (w_{f,k}^i)_{LS}$ if not where $(w_{f,k}^i)_{LS}$ represents the minimisation solution in the least squares sense:

$$(w_{f,k}^i)_{LS} = \frac{z_i^k\left(w_f^M \otimes \ldots w_f^{i+1} \otimes w_f^{i-1} \otimes \ldots \otimes w_f^1\right)}{\left\|w_f^M \otimes \ldots w_f^{i+1} \otimes w_f^{i-1} \otimes \ldots \otimes w_f^1\right\|^2}$$

and that the threshold $Th_{L0}^i$ is given by $$Th_{L0}^i = \frac{\sqrt{\lambda_i}}{\left\|w_f^M \otimes \ldots w_f^{i+1} \otimes w_f^{i-1} \otimes \ldots \otimes w_f^1\right\|}.$$

5. Method for calibrating on-line a direct neural interface according to claim 3, characterised in that q=½ and that the elements $w_{f,k}^i$ resulting from the minimisation are given by:

$(w_{f,k}^i)_{L0} = 0$ if $k \in \Omega_{i,f}$ and $|(w_{f,k}^i)_{LS}| \leq Th_{L0,5}^i$ $(w_{f,k}^i)_{L0} = \arg\min(h_{0,5}(0), h_{0,5}(B^i \cdot (w_{f,k}^i)_{LS}))$ if $k \in \Omega_{i,f}$ and $|(w_{f,k}^i)_{LS}| > Th_{L0,5}^i$ $(w_{f,k}^i)_{L0} = (w_{f,k}^i)_{LS}$ if not where $h_{0,5}(w_{f,k}^i) = \|z_1^k - w_{f,k}^i(w_f^3 \otimes w_f^2)^T\|^2 + \lambda_i \sqrt{|w_{f,k}^i|}$ and where $(w_{f,k}^i)_{LS}$ represents the minimisation solution in the least squares sense:

$$(w_{f,k}^i)_{LS} = \frac{z_i^k\left(w_f^M \otimes \ldots w_f^{i+1} \otimes w_f^{i-1} \otimes \ldots \otimes w_f^1\right)}{\left\|w_f^M \otimes \ldots w_f^{i+1} \otimes w_f^{i-1} \otimes \ldots \otimes w_f^1\right\|^2}$$

and the threshold $Th_{L0,5}^i$ is given by $$Th_{L0,5}^i = \frac{3}{4}\left(\frac{\lambda_i}{\left\|w_f^M \otimes \ldots w_f^{i+1} \otimes w_f^{i-1} \otimes \ldots \otimes w_f^1\right\|^2}\right)^{\frac{2}{3}}.$$

6. Method for calibrating on-line a direct neural interface according to claim 3, characterised in that q=1 and that the elements $w_{f,k}^i$ resulting from the minimisation are given by:

$(w_{f,k}^i)_{L1} = 0$ if $k \in \Omega_{i,f}$ and $|(w_{f,k}^i)_{LS}| \leq Th_{L1}^i$ $(w_{f,k}^i)_{L1} = \text{sgn}((w_{f,k}^i)_{LS})(|(w_{f,k}^i)_{LS}| - Th_{L1}^i)$ if $k \in \Omega_{i,f}$ and $|(w_{f,k}^i)_{LS}| > Th_{L1}^i$ $(w_{f,k}^i)_{L0} = (w_{f,k}^i)_{LS}$ if not where $(w_{f,k}^i)_{LS}$ represents the minimisation solution in the least squares sense:

$$(w_{f,k}^i)_{LS} = \frac{z_i^k\left(w_f^M \otimes \ldots w_f^{i+1} \otimes w_f^{i-1} \otimes \ldots \otimes w_f^1\right)}{\left\|w_f^M \otimes \ldots w_f^{i+1} \otimes w_f^{i-1} \otimes \ldots \otimes w_f^1\right\|^2}$$

and the threshold $Th_{L1}^i$ is given by $$Th_{L1}^i = \frac{\lambda_i}{\left\|w_f^M \otimes \ldots w_f^{i+1} \otimes w_f^{i-1} \otimes \ldots \otimes w_f^1\right\|}.$$

7. Method for calibrating on-line a direct neural interface according to claim 1, characterised in that the electrophysiological signals are ECoG signals.

* * * * *

UNITED STATES PATENT AND TRADEMARK OFFICE
CERTIFICATE OF CORRECTION

PATENT NO. : 12,059,258 B2
APPLICATION NO. : 17/450601
DATED : August 13, 2024
INVENTOR(S) : Alexandre Moly et al.

It is certified that error appears in the above-identified patent and that said Letters Patent is hereby corrected as shown below:

In the Specification

In Column 2, Line 56, replace "$\underline{X}_u \in \square^{(I_1 \times \dots \times I_N)}$" with --$\underline{X}_u \in \mathbb{R}^{(I_1 \times \dots \times I_N)}$--.

In Column 2, Line 57, replace "$\underline{Y}_u \in \square^{(J_1 \times \dots \times J_M)}$" with --$\underline{Y}_u \in \mathbb{R}^{(J_1 \times \dots \times J_M)}$--.

In Column 3, Line 6, replace "$\underline{B}_u^f \in \square^{(I_1 \times \dots \times I_N) \times (J_1 \times \dots \times J_M)}$" with --$\underline{B}_u^f \in \mathbb{R}^{(I_1 \times \dots \times I_N) \times (J_1 \times \dots \times J_M)}$--.

In Column 3, Line 7, replace "$\underline{\beta}_u^f \in \square^{(J_1 \times \dots \times J_M)}$" with --$\underline{\beta}_u^f \in \mathbb{R}^{(J_1 \times \dots \times J_M)}$--.

In Column 6, Line 37, replace "$\underline{X} \subset \square^{I_1 \times \dots \times I_N}$ where $\square$" with --$\underline{X} \subset \mathbb{R}^{I_1 \times \dots \times I_N}$ where $\mathbb{R}$--.

In Column 7, Line 11, replace "$\underline{Z} \in \square^{I_1 \times I_2 \times \dots \times I_M}$" with --$\underline{Z} \in \mathbb{R}^{I_1 \times I_2 \times \dots \times I_M}$--.

In Column 7, Line 35, replace "$\underline{XY}_u \in \square^{I_1 \times I_2 \times I_3}$" with --$\underline{XY}_u \in \mathbb{R}^{I_1 \times I_2 \times I_3}$--.

In Column 7, Lines 45 and 46, replace "$\min_{\underline{XY}_u} \|\underline{XY}_u - \underline{\widehat{XY}}_u\|^2$ with $\underline{\widehat{XY}}_u = \theta_f w_f^1 \circ w_f^2 \circ w_f^3$" with --$\min_{\underline{XY}_u} \|\underline{XY}_u - \underline{\widehat{XY}}_u\|^2$ with $\underline{\widehat{XY}}_u = \theta_f w_f^1 \circ w_f^2 \circ w_f^3$--.

In Column 8, Line 3, replace "$\left(\underline{z}_1^1 | \dots | \underline{z}_1^{I_1}\right) \in \square^{I_1 \times I_2 \times I_3}$" with --$\left(z_1^1 | \dots | z_1^{I_1}\right) \in \mathbb{R}^{I_1 \times I_2 \times I_3}$--.

Signed and Sealed this
Nineteenth Day of November, 2024

*Katherine Kelly Vidal*

Katherine Kelly Vidal
*Director of the United States Patent and Trademark Office*

CERTIFICATE OF CORRECTION (continued)
U.S. Pat. No. 12,059,258 B2

In Column 8, Line 25, replace "$\underline{\mathbf{B}}_u^f \in \square^{(I_1 \times ... \times I_N) \times (J_1 \times ... \times J_M)}$ and a bias tensor $\underline{\beta}_u^f \in (J_1 \times ... \times J_M)$" with --$\underline{\mathbf{B}}_u^f \in \mathbb{R}^{(I_1 \times ... \times I_N) \times (J_1 \times ... \times J_M)}$ and a bias tensor $\underline{\beta}_u^f \in \mathbb{R}^{(J_1 \times ... \times J_M)}$--.

In Column 12, Lines 20 and 21, replace "$\underline{\mathbf{B}}_u^f \in \square^{(I_1 \times ... \times I_N) \times (J_1 \times ... \times J_M)}$ and a bias tensor $\underline{\beta}_u^f \in \square^{(J_1 \times ... \times J_M)}$" with --$\underline{\mathbf{B}}_u^f \in \mathbb{R}^{(I_1 \times ... \times I_N) \times (J_1 \times ... \times J_M)}$ and a bias tensor $\underline{\beta}_u^f \in \mathbb{R}^{(J_1 \times ... \times J_M)}$--.

In Column 13, Line 58, replace "$\underline{\mathbf{X}}_u \in \square^{(I_1 \times ... \times I_N)}$" with --$\underline{\mathbf{X}}_u \in \mathbb{R}^{(I_1 \times ... \times I_N)}$--.

In Column 13, Line 60, replace "$\underline{\mathbf{Y}}_u \in \square^{(J_1 \times ... \times J_M)}$" with --$\underline{\mathbf{Y}}_u \in \mathbb{R}^{(J_1 \times ... \times J_M)}$--.

In Column 13, Line 62, delete "(220).".

In Column 14, Lines 8 and 9, replace "$\underline{\mathbf{B}}_u^f \in \square^{(I_1 \times ... \times I_N) \times (J_1 \times ... \times J_M)}$ and a bias tensor $\underline{\beta}_u^f \in \square^{(J_1 \times ... \times J_M)}$" with --$\underline{\mathbf{B}}_u^f \in \mathbb{R}^{(I_1 \times ... \times I_N) \times (J_1 \times ... \times J_M)}$ and a bias tensor $\underline{\beta}_u^f \in \mathbb{R}^{(J_1 \times ... \times J_M)}$--.

In the Claims

In Column 14, Lines 11-12, Claim 1 delete "($240_1$, $240_1$, ... $240_M$).".